United States Patent [19]

Saurino

[11] 4,321,277

[45] Mar. 23, 1982

[54] GERMICIDAL USE OF COMPOSITIONS CONTAINING CERTAIN QUATERNARY AMMONIUM COMPOUNDS

[75] Inventor: Vincent R. Saurino, Boca Raton, Fla.

[73] Assignee: Research Lab Products, Inc., Palm Beach, Fla.

[21] Appl. No.: 118,312

[22] Filed: Feb. 4, 1980

Related U.S. Application Data

[63] Continuation of Ser. No. 966,311, Dec. 4, 1978, abandoned, which is a continuation of Ser. No. 783,757, Apr. 1, 1977, abandoned, which is a continuation of Ser. No. 558,654, Mar. 17, 1975, abandoned, which is a continuation of Ser. No. 317,225, Dec. 21, 1972, abandoned.

[51] Int. Cl.³ ............................................. A61K 31/14
[52] U.S. Cl. .................................... 424/329; 424/341; 424/DIG. 14
[58] Field of Search ................ 424/329, DIG. 14, 341

[56] References Cited

U.S. PATENT DOCUMENTS

| | | | |
|---|---|---|---|
| 3,219,525 | 11/1965 | Berkow | 424/229 |
| 3,282,776 | 11/1966 | Kitzke et al. | 424/229 |
| 3,349,033 | 10/1967 | Zuccarelli | 252/8.75 |
| 3,594,468 | 7/1970 | Saurino et al. | 424/25 |
| 3,624,224 | 11/1971 | Wei et al. | 424/28 |
| 3,730,960 | 5/1973 | Wei et al. | 424/78 |
| 4,021,537 | 5/1977 | Saurino | 424/54 |

FOREIGN PATENT DOCUMENTS 1301316 12/1972 United Kingdom .

OTHER PUBLICATIONS

Chemical Abstracts 69:99294h (1968).
Chemical Abstracts 60:16386f, 1964.
Chemical Abstracts 57:52748g, 1962.

Primary Examiner—Leonard Schenkman

[57] ABSTRACT

The present invention relates to new and improved germicidal compositions having spermicidal properties comprising of a major amount of a mixture of n—$C_{12-18}$ alkyl dimethyl benzyl ammonium halides and n—$C_{12-14}$ alkyl dimethyl ethylbenzyl ammonium halides and a minor amount of a wetting agent selected from the group consisting of non-ionic, cationic and/or amphoteric surfactants and mixtures thereof.

Spermicidal-germicidal compositions of the present invention possess new, improved and unexpected properties, particularly with respect to being biologically active against a wide range of organism including the venereal type organisms such as *Neisseria gonorrhea*, *Treponema pallidum* and other spirochetes, *Hemophilus ducreyii*, flagellates, such as *Trichomonas vaginalis* and related organisms. The compositions of the present invention have been found to exhibit spermicidal properties and, therefore, are particularly useful as a contraceptive. They are non-irritating towards vaginal tissues.

4 Claims, No Drawings

GERMICIDAL USE OF COMPOSITIONS CONTAINING CERTAIN QUATERNARY AMMONIUM COMPOUNDS

This is a continuation of application Ser. No. 966,311 filed Dec. 4, 1978, which is a continuation of application Ser. No. 783,757 filed Apr. 1, 1977, which is a continuation of application Ser. No. 558,654 filed Mar. 17, 1975, which is a continuation of application Ser. No. 317,225 filed Dec. 21, 1972, all now abandoned.

BACKGROUND OF THE INVENTION

A variety of germicidal compositions are known to the art. A particularly effective such composition, which also is a spermicide, is the subject of U.S. Pat. No. 3,594,468, said composition comprising a mixture of 2-[(2-hydroxy-5-nonyl-benzyl)-methyl-amino]ethane sulfonic acid or a salt of said acid and 2{[3-(dimethyl-aminomethyl)-2-hydroxy-5-nonyl benzyl]methyl-amino}ethane sulfonic acid or a salt of said acid. Compositions of the present invention, which are totally different from the compositions of this patent, are spermicidal and germicidal active materials which are effective against the same range of organisms at generally lower concentrations and possess additional desirable properties such as being milder to inflamed tissues.

SUMMARY OF THE INVENTION

The present invention relates to biostatic and biocidal compositions. More particularly, it is concerned with compositions which are effective in the inhibiting of (biostatic) and killing of (biocidal) a wide range of gram-positive and gram-negative organisms. The compositions also possess spermicidal properties making them particularly useful as a contraceptive and for controlling, preventing and/or curing infection with venereal disease organisms, e.g., *Neisseria gonorrhea* and *Treponema pallidum*. The compositions of this invention may be formulated into a wide range of other end products and uses, among which are germicidal cleaning compositions for hospitals and the like, compositions for the control of mildew, algae and the like, paints which will control microbial corrosion and cosmetics such as shaving creams and skin creams to control staphylocci in lesions.

The compositions of the present invention comprise a mixture of components (A) and (B), as hereinafter defined.

Component A is a synergistic mixture of two selected but dissimilar cationic quaternary ammonium halide designated compounds (1) and (2) ordinarily in proportions of 5–95% of (1) to 95–5% of (2), preferably 30 to 80% of (1) with 70–20% of (2) and especially a 50—50 mixture. Compound (1) is an (n-$C_{12-18}$ alkyl) dimethyl benzyl ammonium chloride and compound (2) is an (n-$C_{12-14}$ alkyl) dimethyl ethylbenzyl ammonium chloride.

Component B is a surfactant or wetting agent selected from the group consisting of cationic, amphoteric and/or non-ionic surfactants and preferably a non-ionic surfactant which is pharmaceutically acceptable and which is compatible with the component mixture (A), particularly preferred are octyl-phenoxy-polyethoxy-ethanol and isooctyl-phenoxypolyethoxy-ethanol.

The following are particularly suitable as compounds (1) and (2): (1) n-alkyl (60% $C_{14}$, 30% $C_{16}$, 5% $C_{12}$, 5% $C_{18}$) dimethyl benzyl ammonium chloride and (2) n-alkyl (68% $C_{12}$, 32% $C_{14}$) dimethyl ethyl benzyl ammonium chloride. As indicated above, compounds (1) and (2) can be admixed in various proportions such that one of said compounds is present in amounts of from 5% to 95% and the other compound making up the balance, and preferably they can be present in amounts of 30–80% of (1) and 70–20% of (2) or still more preferred is when compounds (1) and (2) are present in essentially equal amounts.

Component B is a surfactant or wetting agent selected from the group of cationic, amphoteric and/or non-ionic surfactants and should be selected for its compatibility with component A. Component A is not generally compatible with anionic wetting agent. Compatibility is judged by the absence of phase separation when the materials are mixed.

Cationic wetting agents, if used, should be different from the quaternary components making up component A, and can include fatty amine-alkylene oxide reaction products such as the "Ethomeens"; alkyl oxazolidenes prepared by condensing fatty acids with a β-amino alcohol such as 2-methyl-2amino 1,3-propanediol and salts thereof; substituted imidazolines formed by reacting fatty acids with alkyl diamines. Typical cationic wetting agents also include "Amine 220", "Alro" amines, "Alkaterge"-O, "Miranol" and "Catiosan", all of which are commercially available surfactants.

The amphoteric wetting agents include condensation products of (1) amino and carboxy compounds, (2) amino and sulfonic esters, (3) amino and alkane sulfonic acids (4) amino and aromatic sulfonic acids, and the like; such as N-dodecyl n:n dimethyl betaine; dodecyl amino propionic acid and their alkali metal salts, etc.

The nonionic wetting agents which are preferred include condensation reactions of alkylene oxide such as ethylene oxide and/or propylene oxide with fatty alcohols, fatty acids, alkyl phenols such as condensation products of octyl or nonyl phenol and ethylene oxide commercially available under the following trade names: "Triton X-100", "Igepal" CA-630 and 710, "Igepal" CO, "Synthetics" B-79, "Neutronyx". Still other nonionic surfactants which can be used include polypropylene glycolethylene oxide condensation products available under the trade name of "Pluronics" such as L-64 and F-68, etc., or the sorbitan esters of fatty acids and their ethylene oxide derivatives which are available commercially under the trade names of "Spans" and "Tweens" and include sorbitan monostearate (Span 60), sorbitan monoleate palmitate (Span 40), sorbitan monolaurate (Span 20) and the "Tweens" such as polyoxyethylene sorbitan monostearate (Tween 61), polyoxyethylene sorbitan tristearate (Tween 65), polyoxyethylene sorbitan trioleate (Tween 85) and the like. Particularly useful is isooctyl-phenoxy-polyethoxy ethanol, especially for spermicidal-germicidal compositions Triton X-100 is a water soluble octylphenoxy ethanol containing 10 moles of ethylene oxide ($OPE_{10}$).

The surfactants or wetting agent component B comprises a minor proportion of the composition of the present invention and generally does not exceed 20% of the total of components (A) and (B). It is preferred to use at least about 0.25% of component B based on the weights of components A and B. Preferably this amount is 10%. The ingredients in the present composition are individually commercially available.

The compositions of the present invention have been found to be biologically active against a wide range of organisms including the veneral type organisms such as *Neisseria gonorrhea, Taponema pallidum* and other spirochetes, *Hemophilus ducreyii*, flagellates, such as *Trichomonas vaginalis* and related organisms. The compositions of the invention are particularly effective against *Staphylococcus aureus* and as set forth below screening has been carried out using USDA Strain ATCC No. 6538 of this organism along with *Salmonella choleraesuis* ATCC No. 10708 and *Pseudomonas aeruginosa* ATCC No. 15442. They are also extremely effective spermicides for long periods of time. They may be compounded for application with known carriers in dosage forms such as tablets, capsules, suppositories, powders, jellies, liquids, aerosol sprays and microencapsulations. They can be used in or on fabrics, and various solid surfaces such as metals, etc. to prevent irritation and corrosion and staining.

The active ingredients described for various applications can be diluted or otherwise mixed with solvents, diluents, dispersants, wetting agents, carriers and the like. For example, the active ingredients can be compounded in a stock solution which can then be diluted further with suitable materials for any desired application formulations such as liquids, jellies, creams, tablets, etc.

A wide range of inert solvents, dispersants and/or diluents may be used, both in stock solution and in dosage form products, among which notably are the lower alkanols, e.g., 1 to 20 carbon atoms, such as methyl alcohol, ethyl alcohol, isopropyl alcohol, butyl alcohol, dodecyl alcohol and the like. Other solvents may be used along or with the aforesaid alcohols, such as Butyl Cellosolve and the like. Furthermore, water, preferably distilled and/or demineralized, may also be used as a solvent or diluent, although as demonstrated below the composition is also effective in hard water. Many solid inert ingredients which may act as carriers or diluents are known in the art and include such materials as carboxy methyl cellulose, starches, salt, sodium bicarbonate, talc, sugar, dry milk solids and the like. The choice of carriers, solvents and/or diluents is made according to the way in which the products is to be stored and used. For medical application carriers and diluents should be selected from pharmaceutically acceptable materials; however, for other uses, e.g., cleaning and paint formulations, other materials may be used.

As noted above, the present compositions may be used in a wide range of end products and for a wide range of applications. For many applications, the concentration of the active ingredients is not critical. For example, the present compositions are quite effective against a broad range of organisms found in homes and hospitals either undiluted or in dilutions such as 1 to 20 or 1 to 200 and even as weak as 1 to 3000 (weight-/volume). For other applications, such as application to the body, the concentration of active ingredients would ordinarily be limited to that necessary for the particular therapy intended, and with a view to avoiding side effects and irritation to the part of the body to be treated. For convenience, in handling, it is preferable to form a stock solution of the active ingredients (components A and B) which may be further compounded and/or diluted for various products.

A type example of a composition of the present invention is presented below and identified as a Spermicidal-Germicidal Compound A (SGCA); it is shown in both undiluted and diluted form.

|  | SPERMICIDAL-GERMICIDAL COMPOUND A (SGCA) | % | PPM |
|---|---|---|---|
| COMPONENT A | (1) n-Alkyl (60% $C_{14}$, 30% $C_{16}$, 5% $C_{12}$, 5% $C_{18}$) dimethyl benzyl ammonium chloride - 25% | 95 | 475,000 |
|  | (2) n-Alkyl (68% $C_{12}$, 32% $C_{14}$) dimethyl ethylbenzyl ammonium chloride - water 50% | 25% |  |
| COMPONENT B | (3) Octyl-phenoxy-polyethoxy-ethanol (surfactant) | 5 100 | 25,000 500,000 |
|  | At 1:500 Dilution Yield: Component A (Active) | 0.0950 | 950 |
|  | Component B-octyl-phenoxy- | 0.0050 | 50 |
|  | polyethoxy-ethanol | 0.1000 | 1000 |

The acute oral toxicity of the concentrated SGCA is 725 mg/kg for white rats. The concentrated SGCA may be considered a primary irritant. At use concentrations, 1000 ppm (anhydrous basis), SGCA is neither a primary irritant nor a sensitizing agent. SGCA and its use diluted solutions possess excellent wetting properties and, because of this, readily penetrates hard to reach external or internal areas of various surfaces such as cracks, crevices, etc., thereby providing rapid contact with the contaminated areas or areas requiring treatment. Effective anti-microbial products can be formulated by diluting said compositions with a suitable diluents in proper proportions. The diluent can be aqueous and/or non-aqueous fluids such as aqueous solutions, water, emulsions, etc.

Illustrated below is the bactericidal activity of SGCA:

Bactericidal Activity

L. Method: Methods of Analyses, AOAC, 11th ed., 1970, pg. 61, Use-Dilution Method
Object: To determine the maximum dilution (Minimum concentrations) effective for practical disinfection. Complete kill against:

---

Bactericidal Activity

L. Method: Methods of Analyses, AOAC, 11th ed., 1970, pg. 61, Use-Dilution Method
Object: To determine the maximum dilution (Minimum concentrations) effective for prac- -continued

| Bactericidal Activity | | | |
|---|---|---|---|
| tical disinfection. Complete kill against: | | | |
| At: | PPM | PPM | PPM |
| *Staphylococcus aureus* ATCC #6538 | 450 | 500 | 950 |
| *Salmonella choleraesuis* ATCC #10708 | 400 | 500 | 950 |
| *Pseudomonas aeruginosa* PRD10 (ATCC #15442) | 550 | 750 | 950 |

These values were determined at 95% confidence level over replicate testing. A minimum performance of 59/60 negative carrier subcultures was required.

2. Method: Phenol Coefficient Method; Method of Analyses, AOAC, 11th ed., 1970, pg. 59

Object: To determine bactericidal levels for disinfectants miscible with water that do not exeert bacteric-static effects that cannot be neutralized by one of three subculture media specified, or overcome by suitable subtransfer procedures.

The Phenol Coefficient, determined as the maximum killing dilution observed, divided by the resistance of the test organism to phenol:

| | At |
|---|---|
| *Staphylococcus aureus* ATCC #6538 | 926 |
| *Salomonella typhosa* ATCC #6539 | 604 |

There are Guaranteed Minimum Phenol Coefficients statistically derived from the observed average Phenol Coefficient at a 95% confidence level.

The effectiveness of SGCA at a dilution of 1:500 in a medium as a bactericidal material using *Staphlococcus aureus* strain ATCC #6538 organisms were studied and the results are presented below in Table I.

TABLE I

I. Bactericidal Study (after 48 hrs. incubation at 37° C.)

| Tube | 1 | 2 | 3 | 4 | 5 | 6 | 7 | 8 | 9 | 10 | Control | % Kill |
|---|---|---|---|---|---|---|---|---|---|---|---|---|
| Series Component A-500 | − | − | − | − | − | − | − | − | − | − | + | 100% |

(+) Growth (−) No Growth (PC) Precipitate Cloud-Made

II. Bacteriostatic Study (after 48 hrs incubation at 37° C.)
Transfer of negative carriers to sterile medium.

| Tube | 1 | 2 | 3 | 4 | 5 | 6 | 7 | 8 | 9 | 10 | Control | % Kill |
|---|---|---|---|---|---|---|---|---|---|---|---|---|
| Series Component A-500 | − | − | − | − | − | − | − | − | − | − | + | 100% |

(NT) No Transfer
Reinoculation of negative tubes with *S. aureus* −4mm loop (after 48 hrs. incubation at 37° C.)

| Tube | 1 | 2 | 3 | 4 | 5 | 6 | 7 | 8 | 9 | 10 | Control | % Kill |
|---|---|---|---|---|---|---|---|---|---|---|---|---|
| Series Component A-500 | + | + | + | + | + | + | + | + | + | + | | |

Precisely the same results were obtained with *Salmonella choleraesuis* ATCC #10708, and *Pseudomonas aeruginosa* ATCC #15442. In addition, the same results were obtained with *Pseudomonas aeruginosa* ATCC #15442 using SGCA diluted 1:500 in hard water (700 ppm) with 10 minutes contact time.

Table 2 shows the effect of omitting component B from SGCA. Tests with S.aurens ATCC #6538.

TABLE 2

| Dilution | active ppm of component A | % kill with component B | % kill without component B |
|---|---|---|---|
| 1/500 | 950 | 100 | 100 |
| 1/1000 | 475 | 100 | 100 |
| 1/1100 | 432 | 100 | 100 |
| 1/1500 | 357 | 100 | 100 |
| 1/2000 | 238 | 100 | 100 |
| 1/2500 | 190 | 100 | 100 |
| 1/3000 | 156 | 100 | 60 |
| 1/3500 | 136 | 90 | 10 |
| 1/4000 | 119 | 80 | 0 |

Table 3 shows the effect of varying the proportions of components (1) and (2) in component A of SGCA. Quantities are stated in percentages.

TABLE 4

| Dilution | Active PPM | % kill with Component B | % kill without Component B |
|---|---|---|---|
| 1/500 | 950 | 100 | 100 |
| 1/1000 | 475 | 100 | 100 |
| 1/1500 | 357 | 100 | 20 |
| 1/2000 | 238 | 90 | 0 |
| 1/2500 | 190 | 70 | — |

Table 4 shows the effect of omitting Component B from SGCA. Tests were with *Pseudomonas aeruginosa* ATCC No. 15442.

TABLE 3

| (1) | 95.0 | 76.0 | 71.0 | 47.5 | 29.0 | 19.0 | — |
|---|---|---|---|---|---|---|---|
| (2) | — | 19.0 | 29.0 | 47.5 | 71.0 | 76.0 | 95.0 |
| Component B | 5.0 | 5.0 | 5.0 | 5.0 | 5.0 | 5.0 | 5.0 |
| % Kill * @ 1/3000 | 60% | 70% | 80% | 100% | 60% | 60% | 60% |

The compositions of the present invention are highly effective and fast acting spermicides, especially for humans and domestic animals such as cattle, even in a very dilute concentration. Their low surface tension is considered helpful, in this regard, because they readily distribute themselves over a surface, providing effective coverage and penetration at low concentration. The compositions of the present invention are effective in a wide range of dilutions. For example, dilution of 1 to 200 or 1 to 1000 or even 1 to 3000 have been found to provide satisfactory results. Furthermore, the compositions may be used as a secondary spermicidal composition, i.e., such as in a douche or suppository at dilutions greatly exceeding 1 to 3000. If desired, smaller dilutions may be used for example, 1 to 50, or concentrated active ingredients with only enough carrier diluents, wetting agents, etc., to provide adequate dispersal of the active ingredients may be used for particular applications, e.g., disinfecting.

The following spermicide study demonstrates the effectiveness of this invention.

Three semen samples obtained from three separate human male donors were tested against SGCA. The following is the procedure followed and the test results obtained.

TEST PROPER

I. SGCA was diluted with saline in the following two different manners:

(A) Spermicide to Saline
1:500
1:1000
1:2000
1:4000
1:8000

(B) A 1:12 dilution of SGCA to saline was then prepared and further diluted with saline to the following: SGCA/Saline—Saline

| Column 1 | 2 |
|---|---|
| 1:500 | (X12) = 1:6000 |
| 1:1000 | " = 1:12000 |
| 1:2000 | " = 1:24000 |
| 1:4000 | " = 1:48000 |
| 1:8000 | " = 1:96000 |
| 1:10,000 | " = 1:120,000 |

Effectively then, each of the above first column dilutions are multiplied by 12 to obtain the final spermicidal dilution, as shown above; column 2. The pH of the diluted spermicide was determined by meter to be 7.1.

II.

(A) All materials were placed in a water bath and brought up to a 37° C. temperature.

(B) (a) 0.2 ml of warm semen was mixed with 1.0 ml of warm spermicide for 10 seconds.

(b) 40 seconds after zero time, 5 fields of each spermicide dilution and spermatozoa were microscopically examined under both high and low power for any evidence of motility.

(c) The same mixture was again examined for any motile forms after 30 minutes incubation.

RESULTS AND CONCLUSIONS

The three donors' spermatozoa all exhibited essentially the same reaction to the spermicide.

No sign of sperm motility was found until spermicidal to saline dilution of 1:96000 was reached. Therefore, the previous dilution of 1:48,000 was effective in that no sign of sperm activity could be found after either 40 seconds or 30 minutes incubation.

III. CONTROLS

Control tests on each semen specimen, for effect of dilution and mixing:

(a) The three semen samples identified as "A", "B" and "C", and the saline were brought up to a temperature of 37° C. in a water bath.

(b) 0.2 ml of semen and 1.0 ml of saline were mixed in a test tube for 10 seconds.

(c) After 40 seconds, one drop of each mixture was examined microscopically under a coverslip. Activity was ascertained to be satisfactory in terms of the original assessment (see Chart A).

(d) The semen/saline mixture was again examined after 30 minutes at 37° C., and activity noted as essentially that of the 40 second assessment, (Chart A).

CHART "A" (SPERM ACTIVITY)

| CONTROL | 40 Seconds | 30 Minutes |
|---|---|---|
| A | 55% Motility | 55% Motility |
| B | 75% Motility | 75% Motility |
| C | 85% Motility | 80% Motility |

| SPECIMEN | AGE | TOTAL COUNT OR DENSITY | MOTILITY | VISCOSITY |
|---|---|---|---|---|
| A | 3 Hrs. | 95 mill/cc | 77% | Liquified |
| B | 3 Hrs. | 50 mill/cc | 80% | Liquidied |
| C | 3 Hrs. | 110 mill/cc | 85% | Liquidied |

| DILUTION | ACTIVITY |
|---|---|
| 1:500 | No Motility |
| 1:1000 | No Motility |
| 1:2000 | No Motility |
| 1:4000 | No Motility |
| 1:8000 | No Motility |
| 1:48,000 | No Motile Forms |
| 1:96,000 | Fail-occasional slight movement. |
| 1:120,000 | Fail-one motile form/5 fields. | pH of Spermicidal Solution = (by pH Meter) - 7.1

In connection with suitable modes of application for combined spermicidal and germicidal results, compositions of the present invention can be used as tablets by forming stock solutions or dilutions thereof, mixed with one or more pharmaceutically acceptable solid inert carriers. Preferably, the carriers used include agents which effervesce on contact with moisture, so as to quickly distribute the active ingredients, say when such tablets come into contact with vaginal fluids. The carriers should preferably be of the water-soluble type so that they ultimately can be removed with water.

Capsules of gelatin or similar substances, which dissolve when in contact with vaginal or other fluids, and release the active components, may be used. Within the capsule, the active ingredients may be cut with pharmaceutically acceptable carrier which may be a solid or a viscous liquid which does not dissolve the gelatin. The rate of solution may be predetermined and controlled by the nature and thickness of the material from which the capsule is made.

The active agents may be incorporated as ingredients of the usual type of suppository, composed of e.g., coco butter (without any protective coating such as in the capsule). The suppository may also contain the aforesaid effervescent but otherwise inert carrier material.

A powder formulation may be made by spraying the diluted concentrate upon a water-insoluble and noneffervescent inert base such as talc, etc., to be used as a dusting powder, etc., from which the active ingredients can exert their protective action.

A water-based type of active vaginal jelly can be made by adding a pharmaceutically acceptable thickening agent, e.g. gum agar, into the diluted concentrate.

A liquid compositipon can be made by dilution of the active ingredients of this invention, in a suitable diluent such as water, to be used as a douche or for other sanitation purposes, either a low pressure or medium pressure, or as a mild pressure spray where large areas of the body are to be treated and/or protected.

The compositions of this invention can be used as aerosol sprays, for surface contact and treatment, or as a douche spray under relatively low pressure, but for greater penetration.

They can be used in microencapsulation form in gelatin or other similar coating materials, and in various degrees of solubility in vaginal and/or other fluids.

The compositions of this invention can be incorporated into woven, knitted and/or non-woven fabrics, and/or combinations thereof. Fabrics thus treated can be used in contact with infected areas, in contact with certain other areas to serve as a mild preventative and/or protective medium, merely as a wiping cloth, etc., or to be as an integral part of intimate clothing.

For spermidical applications, where the spermicide is applied to vaginal tissue, the total amount of active ingredients (dosage) normally should be at least 0.01 grain, but preferably it is desirable that the dosage be at least 0.05 grain per application. Higher dosages of the active ingredients can be used to completely insure spermicidal protection. High concentrations of the present invention, which would be used to achieve high dosage, are non-irritating to vaginal tissues even if said tract is infected. A preferred embodiment of the active ingredients are used in dilutions of about 1 to 200 or 1 to 500 or more and in general no more than one milliliter of a solution of that dilution should be used in any one application. For example, where a spermicidal tablet is intended, the tablet may be compounded by spraying a 1 to 200 dilution of active ingredients (e.g., about 25-75% active ingredients), or in a volatile solvent such as alcohol, onto a mixture of sodium bicarbonate and citric acid, e.g., 30-90 parts and 70-10 parts, respectively. For example, the composition may contain 0.5% active ingredients, 75% sodium bicarbonate and 24.5% citric acid (all by weight). Such a composition may be compressed by known methods into a 20 grain tablet which effervesces on contact with moisture, each tablet thus being proper for one dose (or one treatment). On this bases, therefore, each tablet will actually contain 0.1 grain of the active ingredients.

The compositions of the present invention can be used as bactericidal and germicidal agents on various surfaces without causing corrosion or staining and includes such materials as metallic and non-metallic materials such as ferrous and non-ferrous metals, asphaltic materials, plastics terrazzo, and the like.

What is claimed is:

1. A process for treating the vaginal tract to provide protection against *Neisseria gonorrhea* which comprises contacting it with a safe and effective amount of a germicidal composition containing as the essential active ingredients, 95% of component A, consisting of a mixture of substantially equal proportions of an n-alkyl (5% $C_{12}$, 60%, $C_{14}$, 30% $C_{16}$, 5% $C_{18}$)-dimethyl-benzylammonium chloride and an n-alkyl (68% $C_{12}$, 32% $C_{14}$)-dimethyl-ethylbenzyl-ammonium chloride and 5% of a component B consisting of octyl-phenoxy-polyethoxyethanol containing 10 moles of ethylene oxide.

2. The process of claim 1 wherein the active ingredients are dispersed in an inert medium.

3. The process of claim 2 wherein said inert medium is water.

4. The process of claim 3 wherein the amount of water is at least 1000 parts for each part of said active ingredients.

* * * * *